US005633290A

United States Patent [19]
Frechet et al.

[11] Patent Number: 5,633,290
[45] Date of Patent: May 27, 1997

[54] PORE-SIZE SELECTIVE MODIFICATION OF POROUS MATERIALS

[75] Inventors: Jean M. J. Frechet; Frantisek Svec, both of Ithaca, N.Y.

[73] Assignee: Cornell Research Foundation, Inc., Ithaca, N.Y.

[21] Appl. No.: 456,539

[22] Filed: Jun. 1, 1995

Related U.S. Application Data

[60] Division of Ser. No. 388,721, Feb. 15, 1995, which is a continuation-in-part of Ser. No. 964,405, Oct. 21, 1992, abandoned.

[51] Int. Cl.⁶ .................................................. C08J 9/00
[52] U.S. Cl. ..................... 521/54; 521/134; 521/139; 521/140; 523/218; 523/219; 524/177; 524/578; 502/402; 502/404
[58] Field of Search ........................... 521/50, 54, 134, 521/139, 140; 502/402, 404; 523/219, 218; 524/577, 578

[56] References Cited

U.S. PATENT DOCUMENTS

| 4,663,163 | 5/1987 | Hou et al. | 424/101 |
|---|---|---|---|
| 4,732,887 | 3/1988 | Obanawa et al. | 502/402 |
| 4,814,541 | 3/1989 | Lewis | 585/640 |
| 4,950,635 | 8/1990 | Williams et al. | 502/401 |
| 5,141,806 | 8/1992 | Koontz | 427/243 |
| 5,224,972 | 7/1993 | Frye et al. | 55/18 |
| 5,234,875 | 8/1993 | Han et al. | 502/77 |
| 5,418,284 | 5/1995 | Chang et al. | 525/54.1 |
| 5,428,067 | 6/1995 | Wulff et al. | 523/219 |

*Primary Examiner*—James J. Seidleck
*Assistant Examiner*—Duc Truong
*Attorney, Agent, or Firm*—Bruce F. Jacobs; Diderico Van Eyl

[57] ABSTRACT

A method of pore-size selective chemical modification of materials having pores of about 1 to 1,500 nm is disclosed. The resulting novel porous materials are particularly useful as separation media in chromatography, for selective isolation, adsorption and catalysis.

14 Claims, No Drawings

PORE-SIZE SELECTIVE MODIFICATION OF POROUS MATERIALS

CROSS-REFERENCE TO RELATED APPLICATION

This is a divisional of application Ser. No. 08/388,721 filed on Feb. 15, 1995 now allowed which is a CIP of U.S. Ser. No. 07/964,405, filed Oct. 21, 1992, now abandoned.

BACKGROUND OF THE INVENTION

Size selectivity is one of the leading principles of nature. Cell membranes allow permeation of small molecules in the cell body while the large ones are excluded. A similar principle has been adopted in the membrane technology and it is widely used there. Size exclusion is also one of the often used methods in chromatographic separations. The first paper describing so called "gel filtration," involving the separation of proteins from salt, dates back to 1959. Further progress in size exclusion chromatography was made by Moore, J. C. *J. Polym. Sci.* A2, 842, 1964, who introduced macroporous poly(styrene-co-divinylbenzene) beads and developed gel permeation chromatography.

Porous polymer beads are generally produced by the co-polymerization of only a limited number of monomers and crosslinking agents. The broad spectrum of pore surface chemistries available for such beads is commonly obtained by chemical modification of the basic copolymers rather than by the co-polymerization of a monomer bearing the new group. (Sherrington et al., *Syntheses and Separations Using Functional Polymers,* Wiley, N.Y., 1989.) While in the former process the physical properties of the basic matrix remains unchanged and only its surface may be modified, in the later the functional monomers are partly buried inside the matrix and physical properties of the copolymers change when different polymerization feeds are used. Accordingly, the chemical modification of polymer beads is more frequent than is the direct copolymerization of functional monomers. For example, strong cation- and all anion-exchange resins are currently commercially produced by chemical modification of styrene-divinylbenzene copolymers, while only a weak cation-exchanger is produced by polymerization of a mixture containing acrylic acid.

The extent of modification of a porous polymer is typically controlled by the reaction kinetics, i.e., by concentration of reagent, reaction time and temperature, diffusion, neighboring group effects, etc. During such a modification, reaction of groups exposed in the easily available parts of the porous polymer is preferred. As the reaction proceeds, the groups located in less accessible parts react to a larger extent until all groups available are consumed. The kinetic control of the reaction path allows neither specification of locations that should be modified nor prevention of the reaction of some groups in defined regions of a porous bead. The method only controls the overall reaction conversion, i.e., the average content of modified groups, without defining the location thereof.

A far better approach, however, would be to develop a process to control not only the extent of modification but also the location of the groups undergoing reaction. It is an object of the present invention to do so by development of a porous material containing different size pores which pores can be selectively modified to have different surface properties.

SUMMARY OF THE INVENTION

Accordingly, the present invention is directed to a process which comprises treating a porous material having reactive groups within some of its pores with a modifying agent of a size which penetrates into only certain pores of the porous material, which modifying agent chemically modifies or assists in the chemical modification of the reactive groups only within the pores so penetrated. The porous material has a variety of different pore sizes generally ranging from about 1 to 1500 nm and each porous material has pores of at least two size ranges which are each substantially homogeneously distributed throughout the material.

As used herein, the term "pores" refers to openings of about 1 to 1,500 nm in average diameter which originate from the surface of a body. The term "pores" means those openings present, for example, within a porous bead or the like used for chromatographic separations while expressly excluding those openings, spaces or interstices which exist between two or more surfaces of separate elements which form a more complex body, as exists between fibrous elements or the like in a filter or in the structure of U.S. Pat. No. 5,004,645 and the like.

The surfaces of the pores have surface groups which are reactive groups such as epoxy, alcohol, acetal, aldehyde, chloromethyl, thiol, amine, ester, carboxylic acid and anhydride, amide, oxime, imine, hydrazone, enamine, or oxazoline groups. The reactive groups within the pores determine the reactivity of the surfaces thereof.

The process of the present invention selectively modifies the pores of the porous material by employing a modifying agent which reacts with the reactive groups in certain pores, or catalyzes their reaction with another reagent, to chemically modify the reactive surface groups to different surface groups, thereby changing the surface functionality of the pore surface. For example, hydrophilic reactive groups can be changed to hydrophobic groups and vice-versa, changing the surface functionality of the pore surface.

Selective modification is achieved by using a modifying agent such as a catalyst or reagent which is of a size which permits it to penetrate into only certain sized pores. Once it penetrates into the pores in which it fits, the chemical modification occurs transforming the reactive groups therein to surface groups of a different functionality than the original reactive groups. The pores into which the modifying agent can not penetrate because of size constraints remain unmodified. The resultant porous material contains pores with different surfaces functionalities. The material is permeable to air and liquids both before and after modification.

The process of the present invention also includes the preparation of materials possessing different reactive groups in pores of at least two size ranges by a series of consecutive reactions using modifying agents with different molecular sizes. In this way, a porous material may be produced containing two or more different surface functionalities localized in pores of different sizes. For example, the porous material may be first modified using a relatively low molecular volume modifying agent which transforms all accessible groups in substantially all of the pores from one functionality to another functionality, and then another modifying agent with a larger molecular volume than the first modifying agent is used to penetrate only relatively larger pores, thereby changing the functionality therein. In a consecutive fashion, modifying agents each having relatively larger molecular volumes than the last one employed may be used to change the functionalities only in the pores in which they fit. While this convergent process may employ an unlimited number of different size modifying agents, generally from about 2 to 5 and more preferably from about 2 to 3 different size modifying agents are used. The resultant porous material generally contains pores with about 2 to 5 and more preferably from about 2 to 3 different functionalities. The convergent process can be reversed by starting with a relatively large modifying agent and gradually decreasing the size of the modifying agent in each divergent process step. Alternatively the convergent and divergent process can be combined using, for example, a relatively small molecular volume catalyst in the first reaction step, a relatively large molecular volume catalyst in the second reaction step and modifying agents with molecular volumes therebetween the two used in the first two step in remaining steps. The process variants depend on the porous material, modifying agent, reactive groups and desired product.

The products produced by the process of the present invention comprise porous materials having at least two different pore size ranges, with the pores of one size range having surface groups of one functionality and the pores of another size range having surface groups of a different functionality. For example, pores within the range of 1 up to 5 nm may have hydrophilic groups and pores within the range of more than 5 to 50 nm may have hydrophobic groups. Numerous other combinations are possible with the specific different sizes of the pores being of little importance.

Materials produced by the process of the present invention are useful as separation media in chromatography, as membranes, diagnostic materials, medical devices such as hemoperfusion columns, drug delivery systems, toners, catalysts, reagents, media for growth of biological material, supports, filtering devices, micro reactors, storage devices and other related technologies.

DETAILED DESCRIPTION OF THE PREFERRED EMBODIMENTS

The selection of the porous material and the modifying agent will depend on the desired result. Thus, the porous material may be selected so that it has hydrophobic groups in its pores, which groups can be changed by the modifying agent to be hydrophilic groups in all but the smallest pores. Alternatively, the porous material may be selected so that it has hydrophilic groups within its pores, which can be changed by the modifying agent to be hydrophobic groups in all but certain sized pores. In conjunction with choosing the porous material the modifying agent must also be chosen to produce a certain result. The modifying agent must be chosen so that it is capable of reacting with, or catalyzing, the reaction of the reactive groups in the pores of the porous material. Relatively large (molecular size) modifying agents may be used in situations wherein it is desired to only modify the surface characteristics of the larger pores in the porous material. Alternatively, a relatively small modifying agent may be used in situations wherein it is desired to modify the majority of the pores in the porous material. The degree of chemical modification and the size of pores modified can, by this preselection technique, be controlled to produce a predesigned porous material intended for a particular end use.

A large variety of porous materials may be employed in the process of the present invention, wherein each porous material has pores of at least two different size ranges and all of those pores are substantially homogeneously distributed throughout the material. Suitable porous materials include macroporous polymers such as polymers of glycidyl methacrylate or acrylate; 2-hydroxyethyl methacrylate or acrylate; allyl methacrylate or acrylate; chloromethylstyrene; 4-tert-butoxycarbonyloxystyrene; vinylacetate; vinylacetals; vinyl alcohol, vinylbenzyl alcohol or vinyl phenol and esters or ethers thereof; 4-nitrophenyl acrylate; 2,4,5-trichlorophenyl acrylate; acryloyl succinimide; maleic acid; vinylbenzaldehyde, acrolein, or methacrolein or acetal, imine, oxime, or hydrazone derivatives thereof; crosslinked with any of divinylbenzene; ethylene dimethacrylate or acrylate; diethylene glycol methacrylate or acrylate; divinylpyridine; bis- N-vinyl-2-pyrrolidone; N,N-methylene-bis-acrylamide; or trimethylolpropane trimethacrylate. Other suitable porous materials are based on natural polysaccharides such as cellulose, chitin, agarose, guar, and dextran. The porous material may also be an inorganic oxide such as silica, titania, zirconia, alumina, magnesia, and porous glass. Other suitable porous materials include bonded reactive phase materials prepared by the reaction of an inorganic oxide with a reactive silylation agent such as 1-glycidoxypropyl-trimethoxysilane, vinyltrimethoxysilane, and other silanes. The medium pore size of such porous materials is from about 2 to about 100 nm. The pore size distribution generally ranges from about 1 to about 1500 nm. The porous material may be of any suitable shape such as beaded (spherical), irregular, rod shaped, flat membrane-like or any other continuous shape. These porous materials are either commercially available from sources such as Rohm and Haas, Mitsubishi, Dow, Bio-Rad, and Merck, or may be prepared by techniques known in the art such as disclosed in U.S. Pat. No. 5,130,343, the subject matter of which is incorporated herein by reference.

U.S. Pat. No. 5,130,343 discloses a procedure for manufacturing macroporous polymers wherein the porogenic agent is a solution of a soluble linear polymer in a solvent which is a non-solvent for the macroporous polymer. The process of pore formation disclosed in U.S. Pat. No. 5,130,343 is initiated by a separation of the solid phase from the original single liquid phase, which can be initiated by crosslinking during polymerization, by crosslinking of already existing soluble polymeric chains, or by a precipitation stimulated by a chemical reaction. These phase separation processes are random processes that start at the same time in many places within the original liquid and result in the formation of spherical nuclei. These nuclei grow until they contact each other and build an array with the remaining solvent within the voids of the enlarged nuclei. The array of spherical entities is then sintered to a mechanically strong porous solid using a means relevant to the particular material. The natural randomness of the nucleation results in a random pore distribution within the material. Further, since all of the porogenic material is present in the polymerization mixture prior to the commencement of polymerization, all pores which are formed are uniformly distributed throughout the resultant polymers. Such macroporous polymers as well as porous materials based on natural polysaccharides and inorganic oxides that may be prepared by known techniques, or obtained from numerous vendors, constitute a group of materials with a similar uniform distribution of pores within their respective bodies.

Each porous material contains particular reactive groups within its pores. Depending upon the porous material, the reactive groups can include epoxy, alcohol, acetal, aldehyde, chloromethyl, thiol, amine, ester, carbonate, carboxylic acid, amide, oxime, imine, hydrazone, enamine, oxazoline or carboxylic anhydride groups. The reactive groups will determine which modifying agents need to be used to modify the reactive groups to obtain the desired surface functionality of the pores in the porous material. The final surface functionality depends on the reaction scheme used to produce the final surface groups and to a lesser extent the initial surface groups. Example of suitable reaction schemes are disclosed hereinafter. Surface groups according to the present invention may have functionalities that include hydrophobic, hydrophilic, anion-exchange, cation-exchange, affinity, charge transfer, catalytic and metal ion complexing.

The modifying agents are selected by their size and ability to react with or catalyze the modification of reactive groups in the pores of the porous material. The size of the modifying agent is selected based on the pore sizes of the porous material containing reactive groups to be modified. Suitable modifying agents for larger pores, e.g. greater than about 10 nm, include polymeric catalysts such as poly (styrenesulfonic acid), poly(methacrylic acid), poly(acrylic acid), poly(vinylbenzoic acid), or a peracid thereof; poly (ethyleneimine) and its quaternized derivatives, poly (triethylaminoethyl methacrylate), polyvinylpyridine and its quaternized derivatives, or poly (trimethylaminomethylstyrene) and polymeric reagents including a polymeric carbodimide or similar polymeric coupling agent; a polymeric dimethylaminopyridine or similar acylation agent, polymeric amine or other polymers containing basic substituents. Suitable modifying agents for smaller pores, e.g. about 1 to about 10 nm, include such as sulfuric acid, sodium hydroxide, triethylamine, dimethylaminopyridine. The small pore agents will be capable of modifying not only the small pores but also the large pores.

It is well known that the size of a polymer molecule in solution or its hydrodynamic volume, i.e. the volume it occupies in solution, varies with its molecular weight and with the solvent used. (P. J. Flory, *Principles of Polymer Chemistry*, Cornell University Press, 1953); (G. Allen and J. Bevington, Eds., *Comprehensive Polymer Science*, Pergamon Press, 1989, Volume 2, p. 199)

In the case of the reagent, the reagent reacts with the reactive groups in the pores of the porous material into which it enters to change them chemically into different surface groups. The catalyst on the other hand functions by catalyzing the reaction of the reactive groups with a reagent present in the pores. For example, if the surface of the pores contain reactive epoxy groups and if the catalyst is a polymeric acid in water, the epoxy groups will react with water in a hydrolysis reaction that will transform the epoxy groups into diol groups only when the catalyst is present. In the areas where the polymeric acid catalyst is not present (small pores because of size constraints), the epoxy groups will not react with water since the hydrolysis reaction cannot occur in the absence of the catalyst. After the modification of the desired pores is finished, the catalyst is washed out of the pores and may be reused for a subsequent modification.

A few particular process schemes which are within the scope of this invention are described hereinafter. Though numerous other reaction schemes are possible, the following schemes are shown to illustrate the basic concepts of the present invention. Other reactions and specific Examples are contained in Examples Section hereinafter.

In Reaction Schemes 1A and 1B, a porous material is derived from glycidyl methacrylate. Therefore, the reactive groups are epoxides. In this reaction, a catalyst containing strongly acidic sulfonic groups is used together with water as a reagent to transform the hydrophobic epoxy groups (I) to diol groups (II) which are more polar and hydrophilic.

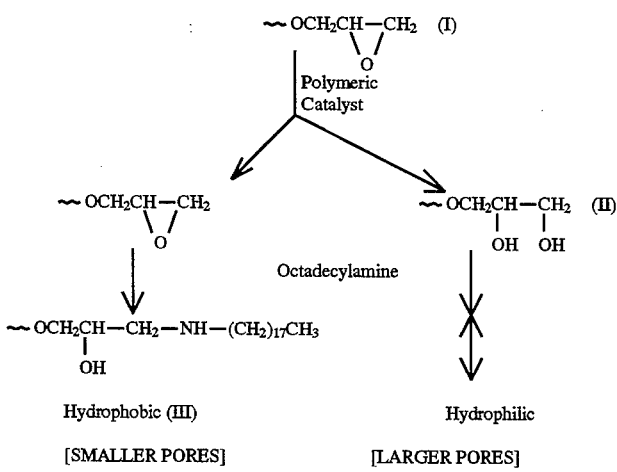

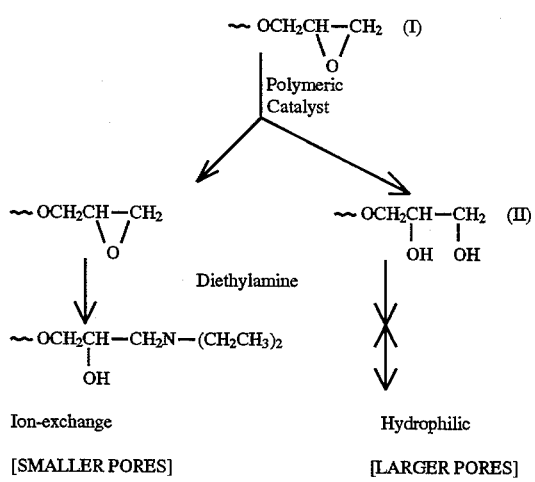

A polymeric catalyst such as poly(styrenesulfonic acid) containing strongly acidic groups, having molecular weight of over one million may be used as the modifying agent. The polymeric acid used for the modification is unable to penetrate the pores having a size smaller than its molecular size. When the hydrolysis is catalyzed with such a polymeric catalyst, the epoxide groups present in pores inaccessible to such a catalyst, i.e. the relatively small pores, remain unchanged and may be used in further steps for other reactions.

If desired, the hydrophobicity of the pores containing the remaining epoxy groups can be increased, for example, by a reaction with relatively small molecules such as higher alkylamines or dialkylamines with alkyl groups containing at least about 8 carbon atoms (such as octadecylamine), alkylarylamines or arylamines. The hydrophobicity and low polarity of the long alkyl chain or aryl group in product III dominates over the polarity of the amino group.

On the other hand, reaction with an amine containing only short alkyl chains such as reaction with diethylamine shown in Reaction Scheme 1B results in product IV with pronounced anion-exchange surface functionality.

In Reaction Scheme 2, the starting porous material is again a copolymer of glycidyl methacrylate. In contrast to the polymeric catalyst, the use of aqueous sulfuric acid as a catalyst in the first reaction step of the convergent approach causes hydrolysis of all epoxide groups present, even those in the smallest pores. The product is treated treated with benzaldehyde under catalysis of a polymeric acid in the absence of water. The large polymeric catalyst does not penetrate the pores smaller than its molecular size and the hydrophilic vicinal diol groups in small pores remain unchanged. The resulting porous material possesses surface functionality opposite to that produced in Reaction Schemes 1; with the small pores being hydrophilic while the large pores are hydrophobic.

Further treatment of the modified porous material with a polymeric acid in presence of water causes hydrolysis of benzylidene acetal groups V to original vicinal diol groups.

REACTION SCHEME 2

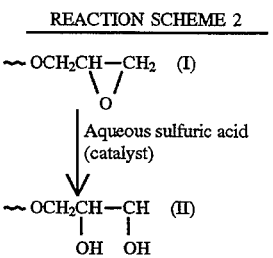

-continued
REACTION SCHEME 2

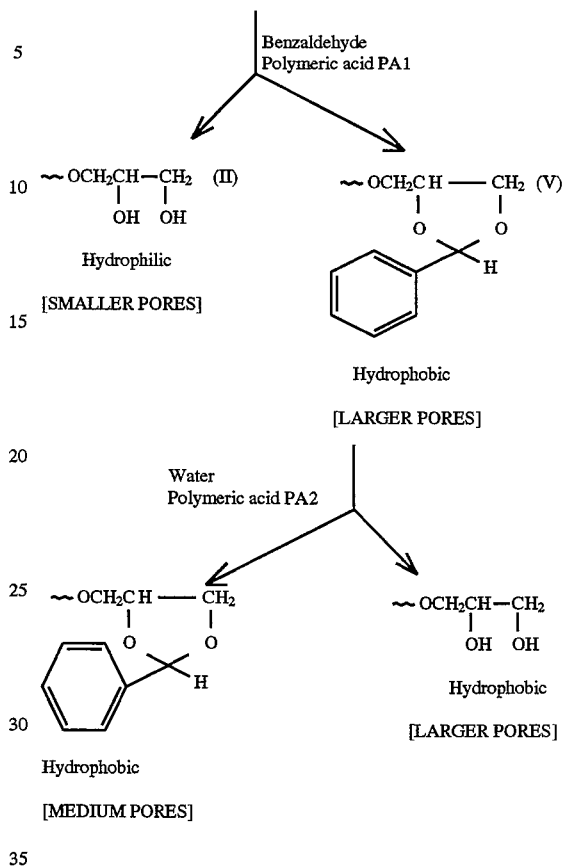

Assuming that the polymeric acidic catalyst PA 1 has molecular volume smaller than PA 2 ($M_{PA\ 1} < M_{PA2}$), the acetal groups located in medium sized pores will survive the treatment and a material appears which has three different zones, i.e. small pores hydrophobic, medium pores hydrophobic and large pores again hydrophilic.

In Reaction Scheme 3, the porous material based on glycidyl methacrylate is again hydrolyzed in presence of aqueous sulfuric acid and the diol groups are reacted with benzaldehyde in the presence of sulfuric acid under anhydrous conditions. The next step is hydrolysis of the benzylidene acetal groups catalyzed by polymeric catalyst. The acetal groups in pores smaller than the size of the catalyst molecule remain unchanged while the others are transformed to a diol, making the larger pores hydrophilic. Finally, the hydroxyl groups in large pores react with chloroacetic acid in the presence of aqueous sodium hydroxide, producing cation exchange groups. The net result is that the smaller pores contain hydrophobic benzylidene acetal groups and the larger pores contain cation exchange groups.

REACTION SCHEME 3

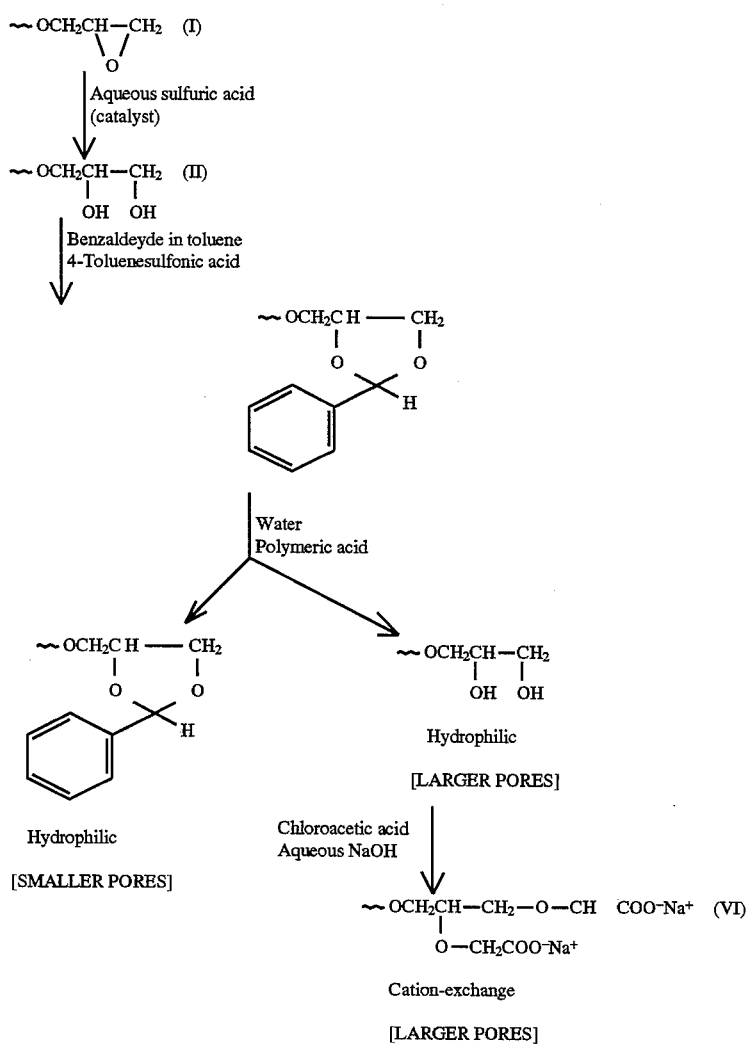

In each of Reaction Schemes 1A, 1B, 2, and 3, the porous material described is based on glycidyl methacrylate. However, the composition of the porous material is not crucial to the final product. Rather, the size of the pores, the pore size distribution and the surface groups within of pores of the starting porous material are more critical to the final product.

In Reaction Scheme 4, the starting porous material is irregular silica. As was the case for Reaction Scheme 1, the polymeric catalyst used as a catalyst in the first reaction step causes hydrolysis of all epoxide groups unless they are hidden in smaller pores inaccessible to the polymeric catalyst. Thus, the larger pores become hydrophilic. In the next step, the remaining epoxide groups react with iminodiacetic acid diethylester producing hydrophobic groups in the smaller pores. The product is then treated with poly(N,N-diethyl-vinylbenzylamine) having a molecular size smaller than that of the polymeric acid used in the first modification step. The ester groups in pores accessible for the said poly(N,N-diethyl-vinylbenzylamine) are saponified to negatively charged carboxylic groups. The small pores remain hydrophobic while the medium size pores have typical ion-exchange properties.

REACTION SCHEME 4

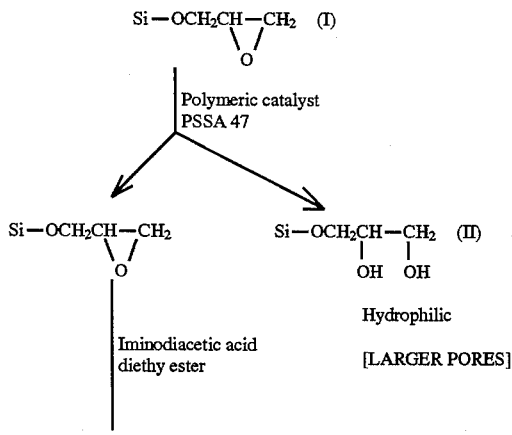

-continued
REACTION SCHEME 4

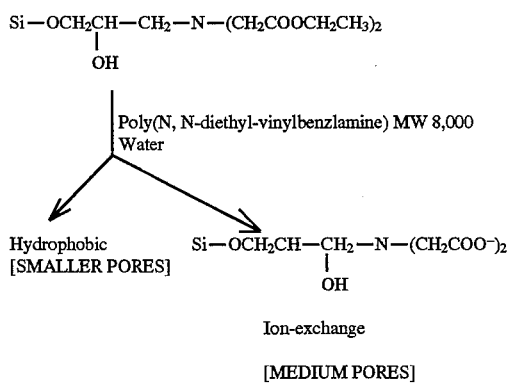

The porous materials produced by the process of the present invention have many uses. They are particularly useful as separation media in liquid chromatography. For example, beads modified in the way depicted in Reaction Scheme 1A may be used in separating drugs from blood plasma. The blood proteins cannot bind to the hydrophobic octadecyl groups in small pores because they cannot fit into those pores. The protein also do not bind to the hydrophilic surface of larger pores into which they fit. On the other hand, smaller drug molecules also do not bind to the hydrophilic surface but they fit into and bind in the smaller pores. They are released when the surrounding liquid is changed to another one which breaks the interaction of the small molecules and the surface hydrophobic groups.

The selectively pore-size modified porous beads are also useful as a packing in devices for blood perfusion after endo- or exogenous poisoning of the living body. The low molecular weight toxic compound bind to groups in smaller pores while the blood particles (ethyrocytes, leukocytes, platelets, etc.) do not penetrate into the beads at all and the blood proteins (albumin, IgG) fit only into the larger hydrophilic pores. The separation of the toxic compounds is very selective as the groups located in smaller pores may be specially designed to bind only the poison molecules. Thus, for removal of heavy metals, such as mercury, cadmium, or lead, the groups in smaller pores are iminodiacetic acid groups, thiol groups, ethylenediamine groups, etc.

The process of present invention is further described in the following Examples which are recited herein as illustrative of the present invention but in no way limit the present invention. All parts and percents are by weight unless otherwise specified.

EXAMPLES 1–3

Uniformly sized porous poly[glycidyl methacrylate-co-ethylenedimethacrylate] (GMA-EDMA) particles 10 μm in diameter were prepared by the modified activated two-step swelling and polymerization method similar to that described in U.S. Pat. No. 5,130,343 except for the addition of a mixture of cyclohexanol and dodecanol as porogen instead of the polymeric porogen. Pore size distribution was controlled by addition of butanethiol to the mixture prior to the last polymerization step. The amount of butanethiol added and the properties of the porous beads are summarized in Table I.

The content of epoxide groups was determine chemically as follows. The beads were dispersed in solution of tetraethylammonium bromide in acetic acid and titrated with 0.1 mol/l perchloric acid solution to the blue-green end point of crystal violet indicator. This technique is described in detail in R. E. Burger and B. P. Geyer, in G. M. Kline, *Analytical Chemistry of Polymers*, Interscience, New York, 1959, p. 124.

Specific surface area and pore size distribution, characterized in the Table I by a median value, were determined by dynamic nitrogen desorption (BET). Pore size distribution and specific pore volume were determined by inverse size-exclusion chromatography (SEC) similar to that used by I. Halasz and K. Martin, *Angew. Chem., Int. Ed. Engl.*, 17 (1978) 901.

TABLE I

Properties of Monosized Poly[Glycidyl Methacrylate-co-Ethylene Dimethacrylate] Porous Beads

| | Example 1 | Example 2 | Example 3 |
| --- | --- | --- | --- |
| Butanethiol added, wt % | 0 | 0.6 | 1.2 |
| Epoxy groups, mmol/g | 2.7 | 2.1 | 2.0 |
| Specific surface area (BET), m$^2$/g | 114.0 | 26.0 | 1.0 |
| Medium pore size diameter (BET), nm | 10.9 | 6.4 | — |
| Specific pore volume (SEC), ml/g | 1.1 | 1.0 | 1.0 |
| Polystyrene exclusion limit (SEC) | 340,000 | 77,000 | 31,000 |

All three kinds of polymer beads (10 g) were suspended separately in 50 ml 0.1 mol/l sulfuric acid and kept at 60° C. for 10 hours while stirred occasionally. All epoxide groups in the beads were hydrolyzed during this procedure as documented by the disappearance of the typical bands of the epoxide groups at 1060, 906, and 852 cm$^{-1}$ and by an increase of the broad hydroxyl band at 3490 cm$^{-1}$ in IR spectrum.

This modification does not exhibit any pore-size selectivity.

EXAMPLES 4–6

The beads containing epoxide groups prepared in Examples 1–3 were hydrolyzed using acids with different molecular weights. The beads containing epoxide groups (0.2 g) were placed in a 50 ml beaker, 10 ml of 1 wt. % aqueous solution of polymeric acid was added and the beaker was sealed with Parafilm. The dispersion was stirred at room temperature for 48 hours. The beads were filtered off on a fritted glass and washed with water to the neutral reaction of the filtrate, washed with acetone and dried. The content of the remaining epoxide groups in the beads was determined by a method described in Examples 1–3. Table II shows the extent of pore-size selective reaction by providing the percentage of remaining epoxide groups located in the polymer beads prepared according to Examples 1, 2 or 3 and used in Examples 4, 5 and 6, respectively, after pore-size sensitive hydrolysis was performed.

TABLE II

Percentage of Remaining Epoxide Groups in Porous Poly[Glycidyl Methacrylate-co-Ethylene Dimethacrylate] Beads after Hydrolysis Catalyzed by a Polymeric Acid
% Remaining Epoxide Groups

| Catalyst | Example 4 | Example 5 | Example 6 |
| --- | --- | --- | --- |
| PSSA 5 | 45 | 57 | 68 |
| PSSA 47 | 64 | 81 | 88 |
| PSSA 400 | 81 | 96 | 97 |
| PSSA 1200 | 89 | 98 | 97 |

PSSA 5 is poly(styrenesulfonic acid) having a molecular weight of 5,000. PSSA 47 is poly(styrenesulfonic acid) having a molecular weight of 47,000. PSSA 400 is poly(styrenesulfonic acid) having a molecular weight of 400,000. PSSA 1200 is poly(styrenesulfonic acid) having a molecular weight of 1,200,000. All the polymeric catalysts had very narrow molecular weight distribution as documented by the polydispersity index, i.e., the ratio of the weight average molecular weight and number average molecular weight $M_w/M_n$, which was less than 1.1 in all polymeric acids used.

Table II shows clearly the size-selectivity of the hydrolysis, the extent of which depends both on the molecular weight of the catalyst and on the pore size distribution of the modified polymer.

The remaining epoxide groups located in smaller pores were used for further modification reactions with octadecylamine or diethylamine according to the Reaction Scheme 1A and 1B. In the former case, the dry beads obtained in Example 4 after hydrolysis catalyzed by poly(styrenesulfonic acid) PSSA 47 were admixed to a melt of 1 g octadecylamine and heated to 70° C. for 16 hours. The mixture was diluted with 2 ml dioxane, mixed 1 hour, and the beads filtered off. Then they were washed consecutively with dioxane, water and methanol and dried. In this way, pores with a size larger than the molecular size of PSSA 47 in water contain hydroxyl groups and are hydrophilic while pores smaller than that limit contain 0.35 mmol/g of attached octadecylamine groups with typical hydrophobic character.

The latter modification proceeded in 2 ml diethylamine using beads from Example 5 hydrolyzed with PSSA 37 and PSSA 5, respectively.

The diethylamino group content was 1.9 and 1.3 mmol/g, respectively. The diethylamino groups located in pores smaller than the molecular volume of the polymeric acids used for the hydrolysis in the first reaction step have an anion exchanger character and thus the pores are more polar and can be used in traditional ion exchange. Pores larger that those modified with diethylamino groups are hydrophilic as they contain only hydroxyl groups resulting from hydrolyzed epoxides.

EXAMPLES 7-8

Diol beads prepared according to Example 1 and 2, respectively, (10 g) were suspended in 200 ml toluene containing 13.4 g benzaldehyde and 0.18 g 4-toluenesulfonic acid. The mixture was refluxed for 48 hours while the water produced by the reaction was continuously removed. The beads were separated, washed consecutively with toluene, acetone and methanol and dried.

Beads containing benzylidene acetal groups (200 mg) were suspended in a 1:1 mixture of dioxane and 0.1 mol/l aqueous sodium sulfate and 10 ml of 1 wt. % aqueous solution of the catalyst was added. The mixture was refluxed for 60 hours. The pore selective modified beads were separated, washed with water and methanol and dried. The extent of the reaction catalyzed by different polymeric acids as determined by IR spectroscopy is summarized in Table III.

TABLE III

Percentage of Remaining Benzylidene Acetal Groups in Modified Porous Poly[Glycidyl Methacrylate-co-Ethylene Dimethacrylate] Beads after Hydrolysis Catalyzed by a Polymeric Acid
% of Remaining Benzylidene Acetal Groups

| Catalyst | Example 7 | Example 8 |
| --- | --- | --- |
| PSSA 5 | 7 | 22 |
| PSSA 47 | 15 | 48 |
| PSSA 400 | 24 | 89 |
| PSSA 1200 | 47 | 95 |

The polymeric acids used in these Examples are identical with those used in Examples 4–6. In Examples 7 and 8 again the extent of the reactions depends both on the molecular weight of the catalyst and on the pore size distribution of the modified polymer.

Beads containing benzylidene acetal groups (200 mg) were suspended in a 1:1 mixture of dioxane and 0.1 mol/l aqueous sodium sulfate and 10 ml of 1 wt % aqueous solution of the catalyst was added. The mixture was refluxed for 60 hours. The pore selective modified beads were separated, washed with water and methanol and dried. The extent of the reaction catalyzed by different polymeric acids as determined by IR spectroscopy is summarized in Table III.

In the carboxymethylation, the previously modified polymer in a 25 ml vial was suspended in a solution 0.4 g sodium hydroxide in 0.8 ml water, and a solution of 0.3 g chloroacetic acid and 0.4 g potassium iodide in 0.2 ml water was added with stirring at room temperature. The temperature was raised to 60° C. and the mixture was stirred for a period 3 hours. The product was transferred in a beaker and thoroughly washed with water several times.

The reaction path is shown in Reaction Scheme 3. Beads from Example 7 were partly hydrolyzed with PSSA 47 as a catalyst. All groups in pores larger than the molecular size of the polymeric acid in water were first transformed into hydroxyl groups and then to carboxymethyl groups. The final product contained again hydrophobic benzylidene groups in pores smaller than the molecular size of the poly(styrenesulfonic acid) PSSA 47 in water while the groups located in larger pores were negatively charged carboxylates with a typical cation exchanger character.

EXAMPLES 9-10

Diol beads prepared according to Examples 1 and 2, respectively, (0.5 g) were suspended in 10 ml dihydropyran containing 0.08 g 4-toluenesulfonic acid. The mixture was refluxed for 8 hours and cooled. The beads were separated, washed consecutively with dioxane, acetone and methanol, and dried.

Beads containing tetrahydropyranyl ether groups (200 mg) were suspended in a 1:1 mixture of dioxane and 0.1 mol/l aqueous sodium sulfate and 10 ml of 1 wt. % aqueous solution of the catalyst was added. The mixture was refluxed for 30 hrs. The pore-selective modified beads were separated, washed with water and methanol, and dried. The extent of the reaction catalyzed by different polymeric acids as determined by IR spectroscopy is summarized in Table IV.

TABLE IV

Percentage of Remaining Tetrahydropyranyl Ether Groups in Modified Porous Poly[Glycidyl Methacrylate-co-Ethylene Dimethacrylate] Beads after Hydrolysis Catalyzed by a polymeric Acid % of Remaining Tetrahydropyranyl Ether Groups

| Catalyst | Example 9 | Example 10 |
| --- | --- | --- |
| PSSA 5 | 18 | 29 |
| PSSA 47 | 25 | 51 |
| PSSA 400 | 33 | 88 |
| PSSA 1200 | 53 | 96 |

The polymeric acids used in this Example are identical with those used in Examples 4–6. Also in Examples 9 and 10, the extent of the reaction depends both on the molecular weight of the catalyst and on the pore size distribution of the modified polymer.

EXAMPLE 11

A copolymer of styrene, 4-vinylbenzyl chloride and divinylbenzene was prepared by a standard suspension polymerization. A mixture containing 25 ml styrene, 25 ml 4-vinylbenzylchloride and 50 ml divinylbenzene (technical grade), 1 g azobisisobutyronitrile, and 100 ml toluene was dispersed in 300 ml of aqueous solution of polyvinyl alcohol. The mixture was stirred for 10 minutes with an anchor shaped stirrer at room temperature. The temperature was then increased to 70° C. and the polymerization continued for 24 hours to afford porous beads with a mean size of 0.18 mm. The porous beads were separated by sedimentation and decanted 3 times in 500 ml distilled water. The washing procedure continued in methanol, toluene, and methanol again, and the beads were dried. The chlorine content in the beads was 5.5 wt % as determined by elemental analysis. The medium pore size was 135 nm and the porosity 54%, both according to mercury porometry measurement. The specific surface area was 120 $m^2/g$ as determined by BET measurements.

The beads containing chloromethyl groups (1 g) were refluxed for 96 hours in 10 ml tetrahydrofuran solution of the sodium salt prepared separately by reaction of sodium hydride (50% w/w in paraffin oil, 0.1 mmol) with a tetrahydrofuran solution of 1 g/l poly(ethylene oxide), (molecular weight 100,000 daltons). After washing with tetrahydrofuran, methanol, water, the beads were transferred to 5 ml 33% aqueous solution of trimethylamine and kept at 50° C. for 10 hours.

The larger pores of the resulting porous polymer are covered with hydrophilic polyethylene oxide chains while the smaller pores contain strong anion exchange quaternary ammonium groups.

EXAMPLE 12

A mixture of 4 ml of freshly distilled methacrolein, 4 ml technical divinylbenzene, 0.8 g benzoylperoxide, and 12 ml cyclohexanol was deaerated by purging with nitrogen and heated in a sealed stainless steel (10 mm I.D.) tube for 20 hours. The polymer block was crushed in a mortar and extracted with toluene, methanol and toluene again using a Soxhlet apparatus.

The porous polymeric material (1 g) was transferred into a 50 ml round bottom flask and 20 ml toluene solution containing 2 g 1,2-dodecanediol and 20 mg 4-toluenesulfonic acid was added. The contents of the flask were refluxed for 60 hours and the released water was removed continuously. The product was washed in the flask by decantation in toluene, methanol, and water. The treatment caused a large decrease of the band at 1720 $cm^{-1}$ in the IR spectrum. This band is characteristic of the aldehyde groups of polymerized methacrolein.

The pore-selective hydrolysis of acetal groups was catalyzed by poly(styrenesulfonic acid) with a molecular weight of 1,200,000 as in Example 7 and a rough estimate of the remaining acetal groups was 50% of the original amount.

The aldehyde groups located in larger pores were reduced by sodium borohydride to hydroxyl groups rendering the larger pores more hydrophilic. At the end, the porous material contained hydrophobic chains in its small pores and hydrophilic groups in its larger pores.

EXAMPLE 13

To 1 g silica in the form of irregular particles having sizes from about 5 to 25 mm, with specific surface area 500 $m^2/g$ (BET), pore volume 0.75 ml/g, and average pore diameter 6 nm, 8 ml of water containing 2 ml 1-glycidoxypropyl-trimethoxysilane was added. The mixture was placed in 75° C. water for 2 hours, the modified silica was filtered off, washed with water and dried. The product contained 0.15 mmol epoxide groups/g.

The particles were treated with 2 ml 1 wt % aqueous solution of poly(styrenesulfonic acid) PSSA 47 (molecular weight 47,300) in the same manner as described in Example 5. After the hydrolysis of the epoxide groups in the larger pores to hydrophilic diol functionality was finished, the content of remaining epoxide groups in the porous particles was 73% of the original amount. Residual epoxides were then reacted with iminodiacetic acid diethyl ester (IADE). The particles (0.2 g) were suspended in 1 ml 10 vol. % solution IADE in dioxane and heated to 70° C. for 24 hours.

Partial hydrolysis of the ethyl acetate groups was catalyzed by poly(N,N-diethylvinylbenzylamine) with a molecular weight of 8,000. The particles were admixed to a 1 wt. % THF- water solution of poly(N,N-diethylvinylbenzylamine) and heated in the water bath 24 hours to 60° C. During this reaction approximately 50% of ester groups were hydrolyzed to produce about 0.1 mmol/g of negatively charged carboxyl groups while leaving about 0.05 mol/g hydrophobic diaminoacetate groups unchanged. The whole reaction path is shown in Reaction Scheme 4.

What is claimed is:

1. A selectively modified material comprising a porous material having pores of at least two different size ranges, with the pores of one size range having surface groups of one functionality and the pores of another size range having surface groups of a different functionality wherein the pores are substantially homogeneously distributed throughout the material.

2. The material of claim 1, wherein the porous material has pores of five different pore size ranges, with the pores of each pore size range having different surface groups with different functionalities compared to all of the other surface groups.

3. The material of claim 1, wherein the functionalities are selected from any of hydrophobic, hydrophilic, anion exchange, cation-exchange, affinity, charge transfer, catalytic, and metal ion complexing.

4. The material of claim 1, wherein the porous material contains pores of two different size ranges with one size range having surface groups of one chemical composition and the pores of another size range having surface groups of a different chemical composition.

5. The material of claim 1, wherein the two different functionalities are hydrophobic and hydrophilic.

6. The material of claim 1, wherein the two different functionalities are of differing polarities.

7. The material of claim 1, wherein the two different functionalities are hydrophobic and cation-exchange.

8. The material of claim 1, wherein the two different functionalities are hydrophilic and anion-exchange.

9. The material of claim 1, wherein the porous material is a polymer selected from the group consisting essentially of glycidyl methacrylate or acrylate; 2-hydroxyethyl methacrylate or acrylate; allyl methacrylate or acrylate; chloromethylstyrene; 4-tert-butoxycarbonyloxystyrene; vinylacetate; vinylacetal; vinyl alcohol, vinylbenzyl alcohol or vinyl phenol and esters or ethers thereof; 4-nitrophenyl acrylate; 2,4,5-trichlorophenyl acrylate; acryloyl succinimide; maleic acid; vinylbenzaldehyde, acrolein, or methacrolein or acetal, imine, oxime, or hydrazone derivatives thereof; crosslinked with any of divinylbenzene; ethylene dimethacrylate or acrylate; diethylene glycol methacrylate or acrylate; divinylpyridine; bis-N-vinyl-2-pyrrolidone; N,N-methylene-bis-acrylamide; or trimethylolpropane trimethacrylate.

10. The material of claim 1, wherein the porous material is an inorganic oxide.

11. The material of claim 1, wherein the inorganic oxide is selected from the group consisting of silica, titania, zirconia, alumina, magnesia or glass.

12. The material of claim 1, wherein the inorganic oxide porous material is a reaction product of the inorganic oxide and a silylation agent.

13. The material of claim 1, the wherein porous material is a natural polysaccharide porous polymer.

14. The material of claim 13, wherein the porous polysaccharide polymer is selected from the group consisting of cellulose, chitin, agarose, dextran, mannan, guar.

* * * * *